United States Patent [19]

Cook, Jr. et al.

[11] Patent Number: 4,484,008

[45] Date of Patent: Nov. 20, 1984

[54] PROCESS IMPROVEMENT FOR DIPHENYL ETHER PRODUCTION

[75] Inventors: James A. Cook, Jr., Barberton; James A. Manner, Akron, both of Ohio

[73] Assignee: PPG Industries, Inc., Pittsburgh, Pa.

[21] Appl. No.: 430,107

[22] Filed: Sep. 30, 1982

[51] Int. Cl.$^3$ .................. C07C 41/16; C07C 41/34

[52] U.S. Cl. .......................... 568/639; 560/65; 560/35; 562/474; 562/435; 260/465 F; 568/62; 568/33; 568/27; 568/585; 564/84; 564/442

[58] Field of Search .......................... 568/585, 639

[56] References Cited

U.S. PATENT DOCUMENTS

| | | | |
|---|---|---|---|
| 3,032,594 | 5/1962 | Towle | 568/585 |
| 3,192,263 | 6/1965 | Spiegler | 568/585 X |
| 3,755,467 | 8/1973 | Darsow et al. | 568/639 X |
| 3,798,276 | 3/1974 | Bayer et al. | 260/612 R |
| 3,839,444 | 10/1974 | Theissen | 260/559 R |
| 3,862,209 | 1/1975 | Theissen | 260/471 R |
| 3,888,932 | 6/1975 | Bayer et al. | 260/612 R |
| 3,928,416 | 12/1975 | Bayer et al. | 260/471 R |
| 3,941,830 | 3/1976 | Theissen | 260/471 R |
| 3,957,852 | 5/1976 | Fujikawa et al. | 260/473 R |
| 3,957,865 | 5/1976 | Rohe et al. | 260/551 R |
| 3,983,168 | 9/1976 | Theissen | 260/501.16 |
| 4,031,131 | 6/1977 | Johnson | 260/473 G |
| 4,063,929 | 12/1977 | Bayer et al. | 71/115 |
| 4,087,272 | 5/1978 | Rohe et al. | 71/120 |
| 4,093,446 | 6/1978 | Bayer et al. | 71/109 |
| 4,104,313 | 8/1978 | Rohe et al. | 568/585 |
| 4,266,082 | 5/1981 | Collin et al. | 568/639 |
| 4,289,909 | 9/1981 | Freenor et al. | 568/315 |
| 4,323,692 | 4/1982 | Tanger | 560/65 |

FOREIGN PATENT DOCUMENTS

| | | |
|---|---|---|
| 104111 | 10/1978 | Canada . |
| 20052 | 12/1980 | European Pat. Off. . |
| 22610 | 1/1981 | European Pat. Off. . |
| 2256142 | 12/1973 | France . |
| 49-1466 | 12/1973 | Japan . |
| 24125 | 2/1980 | Japan ................ 568/639 |
| 1446702 | 8/1976 | United Kingdom . |

OTHER PUBLICATIONS

S/N 51,254–Etherington et al.–filing date Jun. 22, 1979.
S/N 67,508–Etherington et al.–filing date Aug. 17, 1979.

*Primary Examiner*—Bernard Helfin
*Attorney, Agent, or Firm*—Irwin M. Stein; H. Lawrence Jones

[57] ABSTRACT

This invention relates to an improvement in the process of isolating certain diphenyl ethers from an aprotic organic solvent by the addition of a diphenyl ether phase forming amount of water to a reaction mixture comprising a liquid phase of the diphenyl ether dissolved in the solvent.

19 Claims, No Drawings

PROCESS IMPROVEMENT FOR DIPHENYL ETHER PRODUCTION

DESCRIPTION OF THE INVENTION

This invention relates to an improvement in the process of preparing diphenyl ethers. With the advent of the utilization of aprotic organic solvents in the process for preparing diphenyl ethers, certain problems have occurred in regard to the isolation of the diphenyl ether from the reaction mixture, e.g., separating the ether from the aprotic solvent, separating and purifying the diphenyl ether and aprotic solvent when an extraction solvent is used, and disposing of large amounts of waste streams resulting from the use of large amounts of water, extraction solvents and the like.

Various extraction methods have been used to isolate prepared diphenyl ethers from the reaction medium. Among such methods is the addition of an extraneous solvent and large amounts of water to the cooled reaction mixture containing the diphenyl ether. See, for example, U.S. Pat. Nos. 4,266,082; 4,289,909; 4,031,131; 3,941,830; and European Pat. No. 20052. A purpose of the improved process of this invention is to minimize the problems of the prior art processes relating to the isolation of diphenyl ethers from the reaction medium.

It has now been discovered that in the process of producing a diphenyl ether having the graphic formula:

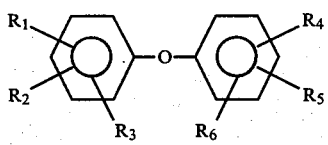

wherein $R_1$, $R_2$, and $R_3$ are each selected from the group consisting of hydrogen, halo, trihalomethyl, $-OCF_3$, $-OCF_2CH(Z)_2$, cyano, $-CO_2R$, phenyl, $-OR$, nitro, $-R$, $-N(R)_2$, $-SH$, $-SOR$, $-SO_2R$, and $-SO_2NH_2$, R is $C_1-C_6$ alkyl and Z is chloro, fluoro, or bromo, and $R_4$, $R_5$, and $R_6$ are each selected from the group consisting of hydrogen, $-R$, nitro, carboxy, $-CO_2R$,

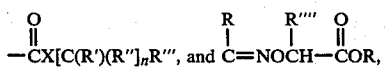

R is $C_1-C_6$ alkyl, R' and R'' are each selected from the group consisting of hydrogen, $C_1-C_6$ alkyl, phenyl and $C_1-C_6$ alkylphenyl, R''' is selected from the group consisting of $-NH_2$, NHR, $-NR_2$, carboxy, and $-CO_2R$, R'''' is hydrogen or methyl, X is $-O-$, $-NH-$, or $-NR''-$ and n is an integer from 1 to 5, with the provisos that no more than two of the substituents $R_1$, $R_2$ and $R_3$ and no more than two of the substituents $R_4$, $R_5$ and $R_6$ are hydrogen and wherein a reaction mixture comprising a liquid phase of said diphenyl ether dissolved in an aprotic organic solvent, is formed, the diphenyl ether can be extracted easily from said aprotic organic solvent by the sequential steps of: (a) adding to the reaction mixture a diphenyl ether phase forming amount of water, thereby to form a first liquid phase having the diphenyl ether as the principal component and a second liquid phase having the aprotic solvent as the principal component, and (b) separating the first liquid phase from the second liquid phase. The process of the present invention provides an easy separation of the reaction solvent from the diphenyl ether in an environmentally sound and cost saving manner.

DETAILED DESCRIPTION

The addition of diphenyl ether phase forming amount of water to a reaction mixture comprising a solution of diphenyl ether in an aprotic organic solvent forms the first liquid phase having the diphenyl ether as the principal component and the second liquid phase having the solvent as the principal component. The amount of water added to the reaction mixture can range from about 0.01 to about 10 percent, e.g., from about 1 to about 10 percent, by weight, preferably from about 1 to about 8 percent, and more preferably from about 2.4 to about 4.8 percent, by weight relative to the weight of diphenyl ether in the reaction mixture. The purity of the water is not essential to the invention, i.e., ordinary tap water, distilled or deionized water can be used. Mixing of the reaction mixture. e.g., stirring or shaking, is preferred when the water is added.

The addition of the aforesaid amount of water to the reaction mixture maintains the reaction mixture in the liquid state except for any solid salt phase which might be present therein. Therefore, it may be necessary to add the water at a temperature up to the boiling point of water at atmospheric pressure or to heat the reaction mixture in order to maintain the liquid state. As long as the liquid state is maintained, however, the temperature during the phase separation is otherwise unimportant. The addition of water to the reaction mixture causes the formation of the first liquid phase and the second liquid phase.

The two liquid phases may be separated by any suitable means such as decanting.

In a specific embodiment of the invention, the reaction of an alkali metal hydroxide with meta-cresol, MCR, in the presence of dimethyl sulfoxide, DMSO, produces in an alkali metal salt formation step an alkali metal salt of MCR. Reaction of the alkali metal salt of MCR with 3,4-dichlorobenzotrifluoride, DBT, in the presence of DMSO then produces in a coupling step a reaction mixture comprising the liquid phase of the diphenyl ether, 3-(2-chloro-4-trifluoromethylphenoxy)-toluene (CTT), ether dissolved in the solvent.

The reaction step of forming an alkali metal salt of MCR also creates water of reaction. Preferably the water of reaction is removed, such as by vacuum distillation or an azeotropic separation, e.g., with toluene, before the coupling step, thereby providing a substantially anhydrous alkali metal salt of MCR prior to the coupling step and therefore providing a substantially anhydrous reaction mixture comprising a liquid phase of said diphenyl ether dissolved in said aprotic organic solvent. The DMSO/MCR mole ratio is typically 3:1 to 2:1. The coupling step is preferably kept anhydrous with enough DMSO to maintain homogeneity, and thereafter as little water as possible is added to give the CTT and DMSO phases.

The reaction mixture comprising the liquid phase of the diphenyl ether dissolved in the solvent has two phases, an organic liquid phase having therein CTT and DMSO and a solid inorganic phase containing a salt of the reaction, i.e. an alkali metal chloride. To the two phase reaction mixture is added the diphenyl ether phase forming amount of water, preferably between 3:1 and 1:1 mole ratio of MCR originally fed:water. Three phases are formed, a distinct organic first liquid phase having CTT as the principal component (CTT phase), a second liquid organic phase having DMSO as the principal component (DMSO phase) and the solid salt phase.

The first liquid phase typically contains about 80 to about 90 percent by weight CTT and about 10 to about 20 percent by weight of DBT, MCR, DMSO and water.

The second liquid organic phase typically contains about 90 to about 95 percent by weight DMSO, about 4 to about 5 percent by weight DBT and MCR and about trace amounts to about 5 percent by weight CTT.

The solid salt phase comprising alkali metal chloride is optionally filtered out at any step after its formation, preferably after the addition of the diphenyl ether phase forming amount of water. While not intending or wishing to be legally bound by theory, it is believed from the evidence at hand that the presence of the water promotes the formation of salt granulates which are easier to filter from the reaction mixture, whereas if the solid salt phase is filtered before the addition of the water, the salt is in a more finely divided form, which is more difficult to filter.

In other specific embodiments, the CTT phase is then distilled to produce a distillate and a substantially pure CTT. In a continuous process, the distillate is recycled to the alkali metal salt formation reaction step. The DMSO phase is then recycled to the alkali metal salt formation reaction step, or separated by distillation into a tops and a substantially pure DMSO. In the continuous process, the substantially pure DMSO can be recovered and then recycled to the alkali metal salt formation reaction step. The tops is also recycled to the alkali metal salt formation reaction step. In a batch process for preparing the diphenyl ether, the recycle of the distillate, the tops and the recovered DMSO is accomplished by storing the materials and adding them to the next batch.

While not intending or wishing to be legally bound by theory, it is believed from the evidence at hand that the addition of the diphenyl ether phase forming amount of water acts in a way to reduce the solubility of the diphenyl ether, e.g., CTT, in the solvent, e.g., DMSO. The water is believed to be acting as an antisolvent.

The description relates to specific embodiment of the invention, but those skilled in the art will recognize that 3,4-dichlorobenzotrifluoride (DBT), meta-cresol (MCR), 3-(2-chloro-4-trifluoromethylphenoxy) toluene (CTT), dimethyl sulfoxide (DMSO) and alkali metal chloride can be substituted therefore by the generic terms reactant 1, reactant 2, diphenyl ether, aprotic organic solvent and, if present, alkali metal halide, respectively.

The addition of the diphenyl ether phase forming amount of water forms two distinct liquid easily separable phases and thus gives the process of this invention the advantages of using little waste water and only one solvent, e.g. DMSO, to be purified and recycled.

The diphenyl ether made by the process of the present invention contains the substituents $R_1$ through $R_6$. $R_1$, $R_2$, and $R_3$ are each selected from the group, hydrogen; halo; e.g. fluoro, bromo and, in a preferred embodiment, chloro; trihalomethyl, e.g. trichloromethyl and, in a preferred embodiment trifluoromethyl; $-OCF_3$; $-OCF_2CH(Z)_2$; cyano, $-CO_2R$, phenyl, $-OR$, nitro, $-R$, $-N(R)_2$, $-SH$, $-SOR$, $-SO_2R$, and $-SO_2NH_2$, R is $C_1$–$C_6$ alkyl and Z is chloro, fluoro, or bromo. $R_4$, $R_5$, and $R_6$ are each selected from the group consisting of hydrogen; $-R$ and in a preferred embodiment methyl; nitro, carboxy,

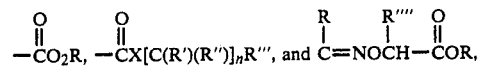

R is $C_1$–$C_6$ alkyl, R' and R" are each selected from the group consisting of hydrogen, $-R$, phenyl and $C_1$–$C_6$ alkyl phenyl; and R''' is selected from the group consisting of $-NH_2$, $-NHR$, $-NR_2$, carboxy, and $-CO_2R$; R'''' is hydrogen or methyl; X is $-O-$, $-NH-$, or $-NR"-$ and n is an integer from 1 to 5, with the provisos that no more than two of the substituents $R_1$, $R_2$ and $R_3$ and no more than two of the substituents $R_4$, $R_5$ and $R_6$ are hydrogen.

In a preferred embodiment of the invention diphenyl ethers have the graphic formula:

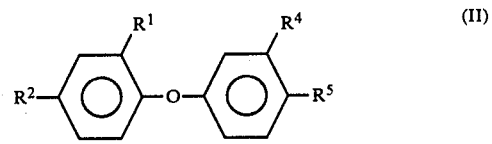

wherein $R^1$ is Z, preferably chloro; $R_2$ is trihalomethyl, preferably trifluoromethyl; $R_4$ is $-R$ preferably methyl,

preferably

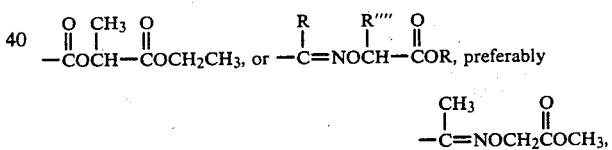

$R_5$ is hydrogen or nitro; and R, R', R", R''', R'''', X, Z and n are as defined within.

The addition of the diphenyl ether phase forming amount of water to the reaction mixture is also useful in extracting the diphenyl ether from the solvent in the preparation of a compound of formula II, e.g., 1-(ethoxycarbonyl)ethyl-5-(2-chloro-4-trifluoromethylphenoxy benzoate, by the addition of an alkali metal hydroxide to the appropriately substituted diphenyl ether, e.g., 5-(2-chloro-4-trifluoromethylphenoxy) benzoic acid, and the subsequent addition of a halogenated substituent containing compound, e.g., 2-chloropropionate.

Examples of the diphenyl ether are those mentioned in the U.S. Pat. Nos. 3,862,209; 3,941,803, and European patent application Nos. 20052 and 22610 and compounds such as 1'-(ethoxy carbonyl)ethyl 5-(2-chloro-4-trifluoromethylphenoxy)-2-nitrobenzoate and 3-(2-chloro-4-trifluoromethylphenoxy) toluene (CTT).

The diphenyl ether is made from reactants which combine to produce the diphenyl ether of the invention and include those compounds having the following graphic formulas: reactant 1:

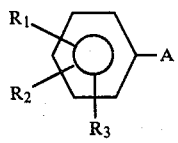

and reactant 2:

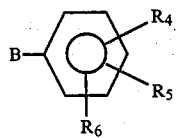

wherein one of A and B is hydroxyl and the other is halo, e.g., fluoro or chloro and $R_1$ through $R_6$ are as described above. Examples of such compounds are 3,4-dichlorobenzotrifluoride (DBT), meta-cresol (MCR), 1-(ethoxy carbonyl)ethyl-5-fluoro-2-nitrobenzoate, 2-chloro-4-trifluoromethylphenol, 3-chloro-4 hydroxybenzotrifluoride, and 5-fluoro-2-nitro-(N,N-dimethylaminoethoxycarbonyl) benzene.

The diphenyl ether has use as a biologically active herbicide or as an intermediate in the preparation of a biologically active herbicide.

The aprotic organic solvents used in the process of the present invention include dimethyl sulfoxide (DMSO), dimethylformamide (DMF), sulfolane, N-methyl-2 pyrrolidone, methyl ethyl ketone, hexamethylphosphoric triamide and the like. Preferably used is DMSO.

The reaction forming the diphenyl ether typically takes place at atmospheric pressure and a temperature between about 120° C. and about 200° C., preferably between about 120° C. and about 160° C. and more preferably between about 130° C. and about 140° C.

The process of the present invention is more particularly described in the following Examples which are intended as illustrative only since numerous modifications and variation therein will be apparent to those skilled in the art. Unless otherwise specified throughout this specification and claims, temperatures are in degrees centigrade and parts, percentages and proportions are by weight.

EXAMPLE 1

To a 5-liter baffled flask, equipped with a thermometer, an electrically driven Teflon blade paddle stirrer and an Allihn condenser, were added 789 parts (7.2 moles) MCR and 1,101 parts DMSO. The temperature in the flask was brought to 45° C. using a Glascol heating mantle connected to a Therm-o-watch temperature controller, and 305 parts (7.56 moles) Pels ® sodium hydroxide were rapidly added with the temperature rising to 95° C. With the temperature controlled at 95° C., a vacuum of 55 millimeters mercury was applied, using an aspirator. At a head temperature of 52°–56° C., water was removed by distillation through a 10-inch Vigreux with reflux head and small fraction cutter. When the water was finally removed, the reaction was stopped at a final pot temperature of 111°–113° C. for a total stripping reaction time of about 11 hours. To the flask was then added 1629.5 parts (7.2 moles) DBT. The reaction proceeded for 11 hours and then over the next 9 hours, the temperature cooled to 30° C.

The addition of about 1 part water to a 20 part sample, with shaking, provided two phases. The further addition of 50 parts of water to the reaction mixture with stirring for 10 minutes produced a two-phase liquid reaction mixture, and a third solid salt phase. The salt phase was filtered to produce a dark yellow CTT phase of 2,258 parts and an amber DMSO phase of 857 parts having the concentrations in Table I as determined by GLC analysis.

TABLE I

|  | CTT Phase | DMSO Phase |
|---|---|---|
| DBT | 6.0 | 0.7 |
| MCR | 1.1 | 3.6 |
| DMSO | 7.9 | 90.6 |
| CTT isomer | 2.2 | 0.3 |
| CTT | 82.8 | 4.9 |
|  | 100.0 | 100.1 |

The yield based on the GLC analysis was 92.6%.

EXAMPLE 2A

To a distillation pot equipped with a 5-inch unpacked column, with heat control at 70 volts, were added 1,130 parts of the CTT phase. The pot temperature was raised successively to 100° C., 120° C. and 140° C., and after a head temperature of 104° C. was reached, the separation was stopped. There were 895.5 parts of substantially pure CTT remaining in the pot, of which 0.52% was m-cresol, 2.23% was CTT isomer and 97.25%, or 870.9 parts, was CTT, as determined by GLC. The distillate, 234.5 parts, contained 1.04% DBT impurity, 18.09% DBT, 1.30% DBT impurity, 74.7% DMSO, 0.58% MCR, 0.29% CTT isomer, and 4.0% CTT.

EXAMPLE 2B

To a distillation pot equipped with a 10-inch Vigreux column, with heat control at 70 volts, were added 1,130 parts of the CTT phase. The pot temperature was raised successively to 87° C., and 128° C. and, after a head temperature of 80° C. was reached, the remaining 899.5 parts of substantially pure CTT contained 0.39% m-cresol, 3.24% CTT isomer and 96.36% CTT, 866.7 parts. The distillate, 227 parts, contained 1.95% DBT impurity, 27.27% DBT, 1.21 DBT impurity, 66.90% DMSO, 0.30% MCR, 0.18% CTT isomer, and 2.8% CTT.

The yield of CTT in Examples 2A and 2B was 84.9%, based on the GLC analysis and the molar amounts of starting materials in Example 1.

EXAMPLE 3

The general procedure and equipment of Example 1 was used to add the same amounts of MCR, DMSO and anhydrous sodium hydroxide to the pot, with the heat applied to get to 98° C. After stirring 50 minutes, with a temperature controlled at 98° C. and 55 mm Hg, the head temperature rose to 73° C., and after the water was removed by distilling, the pressure was adjusted to atmospheric pressure. At 180 minutes, all the DBT was added and the temperature was 80° C. The temperature was controlled between 138° C. and 148° C. initially and then at about 140° C. until the reaction had proceeded for 16 hours. To the reaction mixture was added 100 parts of water and the mixture stirred for 10 minutes. The salts of reaction were filtered; about 25 to 30 parts more water was added to primarily rinse the reactor. The phase separation gave 2,194 parts of a light amber or dark yellow CTT phase and 1,105.5 parts of a dark amber DMSO phase.

The GLC results of the CTT phase were 5.3% DBT, 3.3% DMSO, 1.54% MCR, 2.81% CTT isomer, and 87.0% CTT. The DMSO phase contained 94.8% DMSO, 5.2% MCR and trace amounts of CTT.

EXAMPLES 4A AND 4B

Distillation of the CTT phase of Example 3 was performed according to the general procedure of Example 2 to obtain 859.2 parts of substantially pure CTT and 236.3 parts distillate from 1,097 parts of CTT phase in Example 4A. Example 4B was completed to give from 1,098.2 parts CTT phase, 861.2 parts of substantially pure CTT and 236.5 parts distillate. The total CTT had a combined analysis by GLC of 3.5% CTT isomer, 96.5% CTT and no MCR. The total distillate contained 2.18% DT impurity, 34.3% DBT, 3.3%DBT impurity, 0.4% unknown, 51.7% DMSO, 4.4% CR, 0.3% CTT isomer, and 3.35% CTT.

The results of Examples 1 and 3 demonstrate the process of the invention, and show the excellent separation of the DMSO, with only 4.86% CTT (Example 1) and a trace of CTT (Example 3) concentration in the DMSO phase. The results of Examples 2A, 2B, 4A and 4B demonstrate the separation of the CTT phase into the distillate and the substantially pure CTT.

In order to show the recycle of the distillate, tops (of the DMSO phase separation) and substantially pure DMSO, the following Experiments 5 and 6 were performed.

EXAMPLE 5

The general procedure of Example 1 was followed to prepare CTT except that the DMSO phase (tops and substantially pure DMSO combined) from Example 3 and distillate from Examples 4A and 4B combined were used as the starting materials along with fresh MCR, DBT and DMSO as follows:

| Component | DMSO Phase Parts | Toppings Parts | Fresh Parts | Total Parts |
|---|---|---|---|---|
| MCR | 19 | 15.4 | 754.6 | 789 |
| DBT | 0 | 120 | 1509.5 | 1629.5 |
| DMSO | 471 | 181 | 449 | 1101 |
| NaOH | | | 305 | 305 |
| CTT | 10 | 11.7 | — | 21.7 |
| | 500 | 328.1 | 3018.1 | 3846.2 |

Fresh MCR, 500 parts of DMSO, fresh DMSO, and toppings were charged. The sodium hydroxide was added in 10 to 15 minutes with a pot temperature rise to 80° C. After stirring about 20 minutes, with temperature at 100° C., vacuum applied at 120 mm Hg, with the p at temperature dropping to 95° C. The pressure was successively decreased to 75 mm Hg and 50 mm Hg; and at a final pot temperature of 95° C., the water had been removed in a 2 hour time period. The fresh DBT and toppings were added and after 13 hours' reaction time, after the temperature had dropped to 80° C., 100 parts of distilled water was added and the mixture stirred for 10 minutes and filtered with a #41 Whatman filter paper to give a light amber CTT phase, 2,018 parts, containing 11.4% DBT, 5.8% DMSO, 1.8% MCR, 4.1% CTT isomer and 76.8% CTT and a dark amber DMSO phase, 1,210 parts, containing 89% DMSO, 10.9% MCR and a trace of CTT.

EXAMPLE 6

The general procedure of Example 1 was followed to prepare CTT except that the DMSO phase (tops and substantially pure DMSO combined) from Example 1 and distillate from Examples 2A and 2B combined were used as the starting materials along with fresh MCR, DBT, and DMSO as follows:

| Component | DMSO Phase Parts | Toppings Parts | Fresh Parts | Total Parts |
|---|---|---|---|---|
| MCR | 17.8 | negl. [1 pt] | 771 | 789 |
| DBT | neglig [3.4 pt] | 95.5 | 1,534 | 1,629.5 |
| DMSO | 453 | 234 | 464 | 1,151 |
| NaOH | — | — | 305 | 305 |
| CTT | 24.3 | 7.7 | — | 32.0 |
| | 498.5 | 338.2 | 3,074 | 3,906.5 |

After addition of the sodium hydroxide, the temperature rose to 80° C. and the temperature control was set at 100° C. to 135° C. After more than 70 parts of water were removed, DBT and toppings were added; and 10 hours after the DBT began to be added, the heat and stirrer were stopped at 80° C. (warmed from 40 C.); 100 parts were added with 10 minutes' agitation, filtration and phase separation to give 2,260 parts of a light amber CTT phase containing 8.67% DBT, 6.70% DMSO, 3.36% CTT isomer, 1.28% MCR, and 77.5% CTT. The DMSO phase contained 12.4% water, 0.3% DBT, 81.4% DMSO, 2.8% MCR, 0.03% CTT isomer, and 2.84% CTT.

Although the present process has been described with reference to specific embodiments thereof, it is not intended that such details should be regarded as limitations upon the scope of the invention except as and to the extent that they are included in the accompanying claims.

We claim:

1. In the process of producing 3-(2-chloro-4-trifluoromethylphenoxy)toluene wherein a reaction mixture containing the 3-(2-chloro-4-trifluoromethoxyphenoxy)toluene is formed in dimethylsulfoxide solvent, the improvement which comprises extracting said 3-(2-chloro-4-trifluoromethylphenoxy)toluene from said solvent by the sequential steps of:
   (a) adding to the reaction mixture from about 0.01 to 10 percent by weight relative to the weight of 3-(2-chloro-4-trifluoromethylphenoxy)toluene of a 3-(2-chloro-4-trifluoromethylphenoxy)toluene phase-forming amount of water in the absence of any additional solvents, thereby forming a first liquid phase having 3-(2-chloro-4-trifluoromethylphenoxy)toluene as the principal component and a second liquid phase having the dimethylsulfoxide solvent as the principal component, and
   (b) separating the 3-(2-chloro-4-trifluoromethylphenoxy)toluene phase from the solvent phase.

2. The process of claim 1 wherein the reaction mixture prior to step (a) is substantially anhydrous.

3. The process of claim 1 wherein the reaction mixture containing the 3-(2-chloro-4-trifluoromethylphenoxy)toluene is prepared by the reaction in the presence of the solvent of an alkali metal hydroxide with meta-cresol to form an alkali metal salt of meta-cresol, and the subsequent reaction of 3,4-dichlorobenzotrifluoride or 3-chloro-4-fluorobenzotrifluoride in the presence of the solvent with the alkali metal salt of meta-cresol to form the 3-(2-chloro-4-trifluoromethylphenoxy)toluene and an alkali metal chloride.

4. The process of claim 3 which additionally comprises filtering the alkali metal chloride.

5. The process of claim 3 which additionally comprises the steps of:
   (c) distilling the 3-(2-chloro-4-trifluoromethylphenoxy)toluene phase to produce a distillate and substantially pure 3-(2-chloro-4-trifluoromethylphenoxy)toluene and,
   (d) recycling the distillate to the reaction step wherein, in the presence of the solvent, the alkali metal hydroxide reacts with meta-cresol to form the alkali metal salt of meta-cresol.

6. The process of claim 5, which additionally comprises the step (e) of recycling the solvent phase to the reaction step wherein the alkali metal hydroxide reacts with meta-cresol.

7. The process of claim 5 which additionally comprises:
   (e) the separation of the solvent phase into a tops and substantially pure solvent, and
   (f) the recycle of the substantially pure solvent to the reaction step wherein, in the presence of the solvent, the alkali metal hydroxide reacts with meta-cresol to form the alkali metal salt of meta-cresol.

8. In the process of producing a diphenyl ether having the graphic formula,

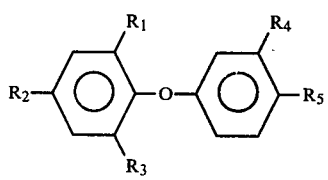

wherein $R_1$ is chloro, $R_2$ is trifluoromethyl, $R_3$ is hydrogen, $R_4$ is methyl, and $R_5$ is hydrogen, wherein a reaction mixture comprising a liquid phase of said diphenyl ether in dimethyl sulfoxide is formed, the improvement which comprises extracting said diphenyl ether from said dimethyl sulfoxide by the sequential steps of:
   (a) adding to the reaction mixture a diphenyl ether phase-forming amount of water, thereby to form a first liquid phase having the diphenyl ether as the principal component and a second liquid phase having the dimethyl sulfoxide as the principal component, and
   (b) separating the first liquid phase from the second liquid phase.

9. The process of claim 8 wherein the reaction mixture prior to step (a) is substantially anhydrous.

10. The process of claim 8 wherein the amount of water added in step (a) is from about 1 to about 10 weight percent, basis the weight of diphenyl ether in the reaction mixture.

11. The process of claim 10 wherein the amount of water added is from about 2.4 to about 4.8 weight percent.

12. The process of claim 8 wherein the diphenyl ether is prepared by the reaction of a first reactant having the graphic formula,

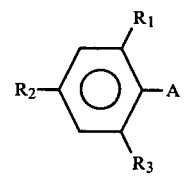

with a alkali metal hydroxide in the presence of dimethyl sulfoxide, thereby to form an alkali metal salt of the first reactant, and the subsequent reaction of said first reactant alkali metal salt in the dimethyl sulfoxide with a second reactant having the graphic formula,

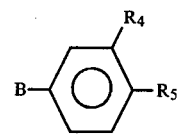

wherein one of A or B is hydroxyl and the other is chloro or fluoro, thereby to form a liquid reaction mixture of dimethyl sulfoxide and diphenyl ether, said reaction mixture containing a solid phase of alkali metal halide.

13. The process of claim 12 wherein $R_1$ is chloro, $R_2$ is trifluoromethyl, $R_3$ is hydrogen, A is chloro or fluoro, $R_4$ is methyl, $R_5$ is hydrogen and B is hydroxyl.

14. The process of claim 13 wherein the solid alkali metal halide is filtered from the reaction mixture before step (a).

15. The process of claim 14 wherein the solid alkali metal halide is filtered from the reaction mixture after step (a).

16. In the process of producing 3-(2-chloro-4-trifluoromethylphenoxy)toluene wherein a reaction mixture containing the 3-(2-chloro-4-trifluoromethylphenoxy)toluene is formed in dimethylsulfoxide, the improvement which comprises:
   (a) reacting an alkali metal hydroxide with meta-cresol in the presence of dimethylsulfoxide to form an alkali metal salt of meta-cresol;
   (b) reacting a material selected from the group consisting of 3,4-dichlorobenzotrifluoride and 3-chloro-4-fluorobenzotrifluoride in the presence of dimethylsulfoxide with the alkali metal salt of meta-cresol to form a reaction mixture of 3-(2-chloro-4-trifluoromethylphenoxy)toluene and alkali metal chloride in dimethylsulfoxide;
   (c) adding to the reaction mixture from about 0.01 to 10 weight percent, relative to the weight of 3-(2-chloro-4-trifluoromethylphenoxy)toluene, of a 3-(2-chloro-4-trifluoromethylphenoxy)toluene phase-forming amount of water in the absence of any additional solvents, thereby forming a first liquid phase having 3-(2-chloro-4-trifluoromethylphenoxy)toluene as the principal component and a second liquid phase having dimethylsulfoxide as the principal component; and
   (d) separating the first phase from the second phase.

17. The process of claim 16 which additionally comprises the steps of:
   (e) distilling the 3-(2-chloro-4-trifluoromethylphenoxy)toluene phase to produce a distillate and substantially pure 3-(2-chloro-4-trifluoromethylphenoxy)toluene; and
   (f) recycling the distillate to step (a).

18. The process of claim 17 which additionally comprises the steps of:
   (g) separating the second liquid phase into a tops and substantially pure dimethylsulfoxide; and
   (h) recycling the substantially pure dimethylsulfoxide to step (a).

19. The process of claim 16 which additionally comprises removing alkali metal chloride from the reaction mixture after step (b).

* * * * *

UNITED STATES PATENT AND TRADEMARK OFFICE
CERTIFICATE OF CORRECTION

PATENT NO. : 4,484,008

DATED : November 20, 1984

INVENTOR(S) : James A. Cook, Jr., et al

It is certified that error appears in the above-identified patent and that said Letters Patent is hereby corrected as shown below:

Claim 1, line 3, "3-(2-chloro-4-trifluoromethoxy-" should be --3-(2-chloro-4-trifluoromethyl- --;

Claim 12, line 5, "a alkali" should be --an alkali--;

References Cited, Foreign Patent Documents, "104111 10/1978 Canada" should be --1041111 10/1978 Canada--.

Signed and Sealed this

Second Day of July 1985

[SEAL]

Attest:

DONALD J. QUIGG

Attesting Officer     Acting Commissioner of Patents and Trademarks